United States Patent
Cook

Patent Number: 6,095,647
Date of Patent: Aug. 1, 2000

[54] OPHTHALMOSCOPE ATTACHMENT

[75] Inventor: Daniel G. Cook, Maple Plain, Minn.

[73] Assignee: Health & Technology, Inc., Minneapolis, Minn.

[21] Appl. No.: 09/394,152

[22] Filed: Sep. 13, 1999

[51] Int. Cl.⁷ ........................................ A61B 3/10
[52] U.S. Cl. ............................................ 351/205
[58] Field of Search ........................ 351/200, 205, 351/211, 212, 216, 217, 244, 245

[56] References Cited

U.S. PATENT DOCUMENTS

| | | | |
|---|---|---|---|
| 3,724,931 | 4/1973 | Nevyas et al. | 351/245 |
| 4,093,359 | 6/1978 | Ketcham | 351/200 |
| 4,196,980 | 4/1980 | Heine | 351/211 |

*Primary Examiner*—George Manuel
*Attorney, Agent, or Firm*—Kinney & Lange, P.A.

[57] ABSTRACT

An ophthalmoscope attachment comprising a mask and mounting means to help focus an individual's direction of sight toward an eyepiece in a housing at a front of an ophthalmoscope. The mask is secured to the front of the housing of the ophthalmoscope by the mounting means. The mask is placed across the front of the ophthalmoscope so that it does not interfere with the eyepiece of the ophthalmoscope when the mask is secured across the front of the housing.

22 Claims, 8 Drawing Sheets

OPHTHALMOSCOPE ATTACHMENT

BACKGROUND OF THE INVENTION

The present invention pertains to an ophthalmoscope. More particularly, the invention pertains to an ophthalmoscope attachment.

Ophthalmoscopes are used by medical personnel to examine the inside of an eye. A standard ophthalmoscope includes a handle, a neck and a housing. The neck extends from the handle at one end and connects to the housing at an opposite end. The handle contains a battery, which is generally rechargeable, to power the ophthalmoscope. The housing contains a lens selection disc and an eyepiece. The lens selection disc alters the lens aligned with the eyepiece which is used to examine the eye. Ophthalmoscopes also include a light source for illumination. A deflecting prism or a perforated angled mirror allows illumination and viewing through the eyepiece of the entire area of the retina, the head of the optic nerve, the retinal arteries and veins, and the vitreous humor.

To properly conduct an eye examination, the patient is instructed to look directly into the light that is emitted from a front of the housing through the eyepiece of the ophthalmoscope. However, young children are typically afraid of the ophthalmoscope and will not look directly at the light or eyepiece. Even if a child cooperates and looks directly at the light, this lasts generally only for a moment or two before the child's attention and line of sight are directed elsewhere. As a result, conducting a thorough examination of a child's eye is extremely difficult, if not impossible.

Children's adverse reaction to the ophthalmoscope is generally a result of their fear and anxiety of the unknown and unfamiliar medical instrument. The appearance of a standard ophthalmoscope is cold and uninviting to a young child. The handle of a standard ophthalmoscope is generally stainless steel and silver in color, while the housing that includes the eyepiece is generally formed of hard plastic and is black in color. The shaft placed between the handle and the housing can be made of either stainless steel or formed hard plastic and is either silver or black, respectively, in color. The standard ophthalmoscope used during medical examinations thus tends to only increase an already fearful and anxious experience for a child.

BRIEF SUMMARY OF THE INVENTION

The invention is an ophthalmoscope attachment that is inviting to children and assists in focusing the child's direction of sight toward a light beam that is emitted from a front of a housing of an ophthalmoscope through an eyepiece. The ophthalmoscope attachment comprises a mask and securing means. The mask is attached by the securing means to the front of the housing of the ophthalmoscope to present a friendly, inviting and familiar appearance to the child looking at the ophthalmoscope. An aperture can also be included and placed through the mask so that it is aligned with the eyepiece of the ophthalmoscope when the mask is secured by the securing means to the front of the housing. The aperture enables viewing of an inside of the eye during the examination.

DETAILED DESCRIPTION

Figure 1:
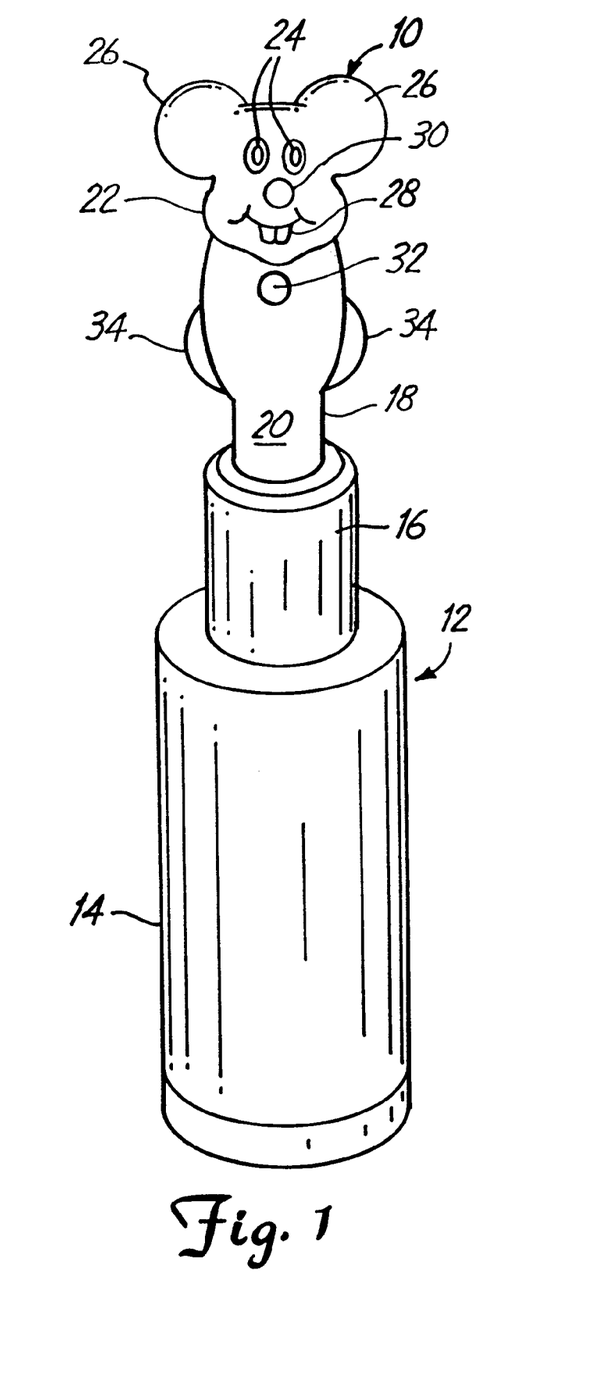
FIG. 1 is a perspective view of a first embodiment of the invention secured to an ophthalmoscope.

A preferred embodiment of an ophthalmoscope attachment 10 is shown in FIG. 1. The ophthalmoscope attachment 10 is used in conjunction with an ophthalmoscope 12 by medical personnel to examine an inside of a patient's eye. The ophthalmoscope 12 includes a handle 14, a neck 16 and a housing 18. The ophthalmoscope attachment 10 is secured to the housing 18 at a front 20 of the ophthalmoscope 12. The ophthalmoscope attachment 10 converts the ophthalmoscope 12 from an intimidating and unfamiliar medical device into an inviting and friendly toy as perceived by the patient.

The standard ophthalmoscope 12 is generally intimidating and uninviting to children. The handle 14 is generally made of stainless steel and is silver in color. The housing 18 is generally formed from hard plastic and is black in color. The neck 16 can be made of either stainless steel or formed hard plastic and is either silver or black in color, respectively.

The sterile, cold and unfamiliar appearance of the ophthalmoscope 12 creates fear or anxiety in a child whose eye is being examined with the ophthalmoscope 12. A proper examination of an inside of the eye requires the child to look directly at the ophthalmoscope 12. This is not likely to occur if the child is afraid or anxious of the device. The ophthalmoscope attachment 10 is used to help calm the child's anxiety and fear of the device. The ophthalmoscope attachment 10 is secured to the front 20 of the housing 18. When the child views the ophthalmoscope 12 during the examination of the inside of their eye, they will see the ophthalmoscope attachment 10, rather than the sterile, unfamiliar, and cold housing 18.

The ophthalmoscope attachment 10 has a mask 22 which is secured to the front 20 of the housing 18. The mask 22 is preferably formed in the shape of an animal face, such as a mouse as in FIG. 1. The mask 22 could also be formed in the shape of another animal, such as a lion, a tiger, or a monkey.

The mask 22 is preferably made of a material that is either dyed or painted to match the characteristics of its shape. For example, the mask 22 as described earlier, could be in the shape of a mouse's face and include a pair of eyes 24, a pair of ears 26, a mouth 28 and a nose 30 that are painted in characteristic colors. Alternatively, the mask 22 can be painted in uncharacteristic or bright colors to aid in drawing the child's attention to the ophthalmoscope attachment 10.

The ophthalmoscope 12 further includes an eyepiece 32 through the housing 18 and a lens selection disc 34 that is contained within the housing 18. The lens selection disc 34 preferably extends on either side of the housing 18 for rotating the disc 34. The eyepiece 32 is used by the examining physician or medical personnel to view the inside of the eye of the patient. The lens selection disc 34 rotates and alters the lens that is aligned with the eyepiece 32 to enable a thorough examination of the eye. The mask 22 is preferably positioned so that it does not interfere with the view through the eyepiece 32, such as above the eyepiece 32 as illustrated in FIG. 1.

A battery is generally contained within the handle 14 to provide power to the ophthalmoscope 12. The battery contained within the handle 14 is generally rechargeable. The battery powers a light source contained within the housing 18 that is used to emit a light beam through the eyepiece 32 to illuminate the eye during the examination.

Figure 2:
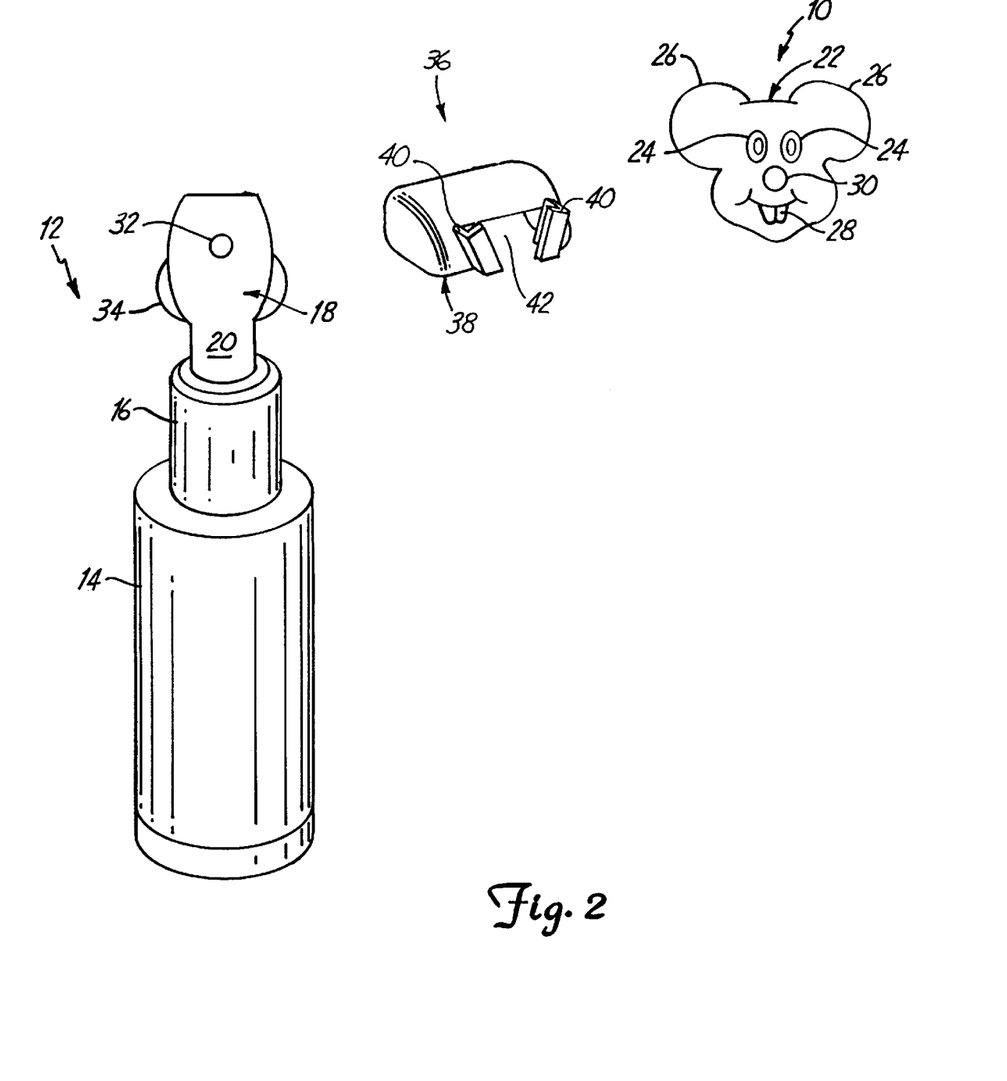
FIG. 2 is an exploded perspective view of the first embodiment of the invention.

FIG. 2 provides an exploded perspective view of the ophthalmoscope attachment 10 and the ophthalmoscope 12. As can be seen in FIG. 2, a standard housing 18 has a gradually curved front section with a generally rectangular top section above the eyepiece 32 and a more circular bottom section that coincides with the lens selection disc 34 below the eyepiece 32. The standard ophthalmoscope 12 has limited if any surfaces upon which the mask 22 of the ophthalmoscope attachment 10 can be removably secured. Mounting means 36 are therefore provided in conjunction with the mask 22 for removably securing the mask 22 to the housing 18.

Mounting means 36 are preferably formed from hard plastic and are black in color to match the color of the housing 18. Mounting means 36 are preferably permanently secured to the housing 18 to provide a platform that the mask 22 can be removably secured to. Mounting means 36 can be formed or shaped in various configurations to provide a platform upon which the mask 22 can be secured.

Mounting means 36 preferably includes a mounting plate 38 that is shaped similar to the general shape of the top section of the housing 18 so as to maintain a similar appearance to the standard ophthalmoscope 12 when the mask 22 is not secured across the front 20. The mounting plate 38 therefore has a generally rectangular shape to fit across the rectangular top section of the housing 18. The mounting plate 38 is preferably secured to the housing 18 by some sort of an adhesive, such as two-way tape or glue. The mounting plate 38 can alternatively be formed as part of a top cover that slides over the top of the housing 18, by use of a fastener such as a screw, or formed as an integral part of the housing 18.

Mounting means 36 also preferably includes a pair of opposed facing walls 40 that extend outward from the mounting plate 38. The walls 40 are preferably closer together at their bottom end and further apart at their top ends, or form part of a V-shape. The mask 22 is then removably secured to the walls 40. The mask 22 is secured to the walls 40 and across the front 20 of the housing 18 when necessary, such as when examining a child, and is removed when not needed, such as when an adult is being examined. Mounting means 36 also includes an opening 42 in the mounting plate 38 as necessary to ensure that the mounting plate 38 does not cover or obscure the eyepiece 32.

Figure 3A:
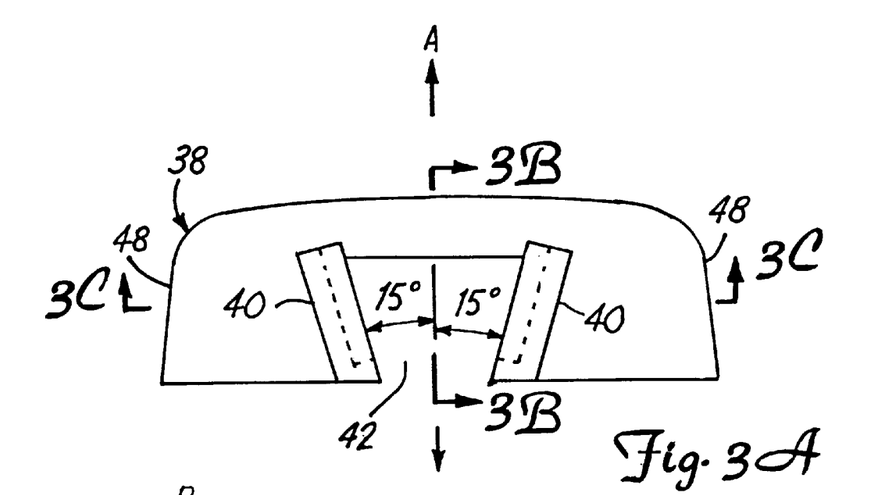
FIG. 3A is a front view of a preferred embodiment of a mounting plate used in the invention.

FIGS. 3A–3D provide a front, side sectional, bottom sectional, and back view, respectively, of a first embodiment of the mounting plate 38. As seen in FIG. 3A, when the mounting plate 38 is permanently placed on the front 20 of the housing 18 it will blend in with the housing 18 to maintain a consistent look to the device. The opening 42 will also ensure that the mounting plate 38 does not effect use of the ophthalmoscope 12 or the field of view through the eyepiece 32.

Figure 3B:
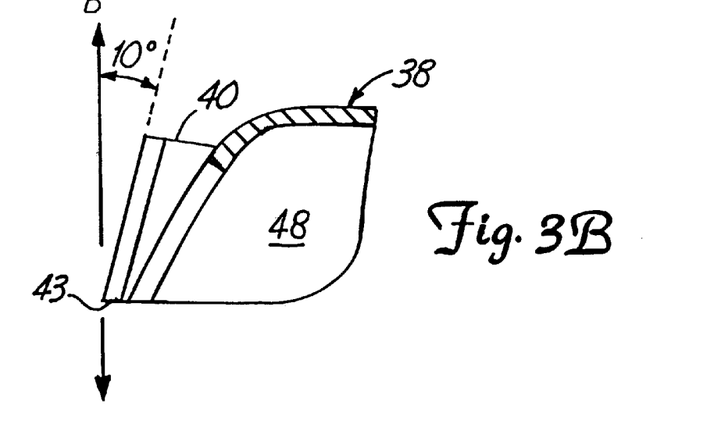
FIG. 3B is a side sectional view of the mounting plate through a section 3B—3B of FIG. 3A.
Figure 3C:
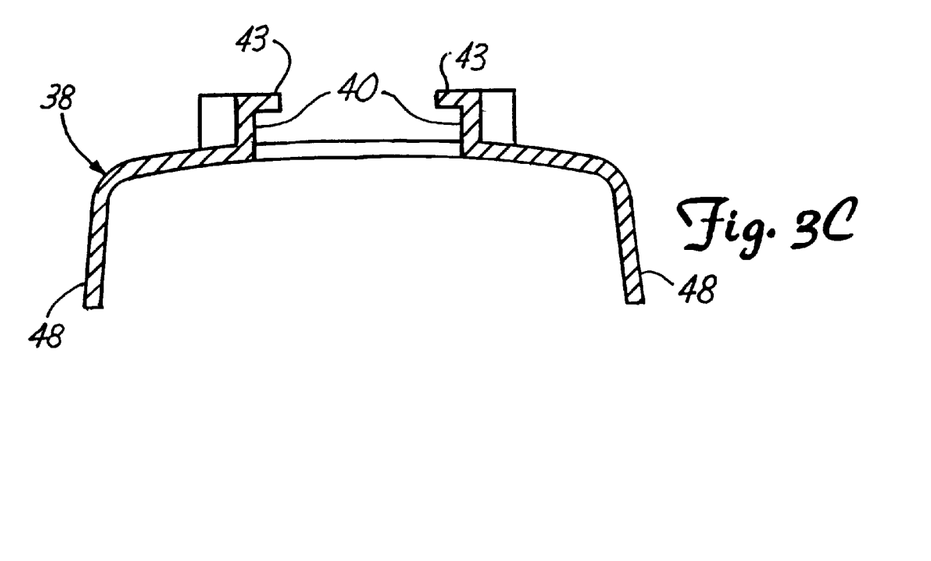
FIG. 3C is a bottom sectional view of the mounting plate through a section 3C—3C of FIG. 3A.

The mounting plate 38 provides the walls 40 upon which the mask 22 can be removably secured. The opposed facing walls 40 are more clearly shown in a side sectional view and bottom sectional view as illustrated in FIGS. 3B and 3C, respectively. FIG. 3B and 3C show the opposed facing walls 40 extending from the front of the mounting plate 38. The walls 40 preferably extend perpendicular to the mounting plate 38. As illustrated in FIG. 3A, the opposed facing walls 40 are slanted toward each other as they run from the top to the bottom of the mounting plate 38 forming a partial V-shape. The walls 40 preferably slant at an angle of approximately 15 degrees with a line A bisecting the mounting plate 38 in FIG. 4A. The walls 40 preferably include a rail 43 that extends inward (or toward the opposed facing wall 40) that is used to mount the mask 22 to the mounting plate 38 and in turn to the ophthalmoscope 12. The rail 43 is more clearly illustrated in the bottom sectional view provided by FIG. 4C. In a preferred embodiment, a top of the walls 40 or the rails 43 tilt back toward the mounting plate 38 at an angle of approximately 10 degrees from a vertical line B. The rails 43 are angled at approximately 10 degrees so that when the ophthalmoscope 12 is used during the examination the child will be able to see the mask 22 attached to the rails 43. The mask 22 will thus appear to face the child as the examining physician or medical personnel places the ophthalmoscope 12 against their face and looks at the child's eye.

The walls 40 preferably extend from the mounting plate 38 a greater distance at the top of mounting plate 38 as compared to the bottom of the mounting plate 38. This results from the gradual slope on the front 20 of ophthalmoscope 12 that is mirrored by the mounting plate 38 to maintain a uniform appearance. The rails 43 preferably extend in from the walls 40 approximately 1.5 millimeters and have a thickness of approximately 1.5 millimeters. A slit, slot, or other geographical shape or void as well as some other fastening technique such as a screw or bolt could also be used in place of the rails 43 for securing the mask 22 across the front 20 of the housing 18. The size of the rails 43 or the angle they create with the vertical line B can also be altered.

Figure 3D:
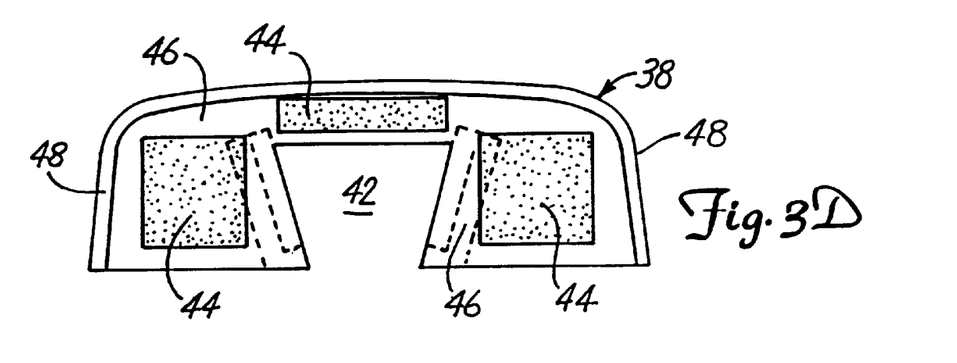
FIG. 3D is a back view of the mounting plate.

Two-way adhesive strips 44 are preferably adhered to a back surface 46 of the mounting plate 38 as illustrated in FIG. 3D. The mounting plate 38 also includes a pair of sidewalls 48 to maintain a completely enclosed appearance to the housing 18 when the mounting plate 38 is attached to the front 20 of the ophthalmoscope 12.

In a preferred embodiment, the mounting plate 38 is formed from hard plastic that is dyed black to match the housing 18. The mounting plate 38 preferably has a height of approximately 14.0 millimeters and mirrors its appearance with the housing 18 as much as possible. The opening 42 in the mounting plate 38 is coincident with the eyepiece 32 to ensure the eyepiece 32 is not covered or partially obscured. The adhesive strips 44 are preferably polyvinyl chloride foam coated with adhesive on both major surfaces to secure the mounting plate 38 to the housing 18.

Figure 4A:
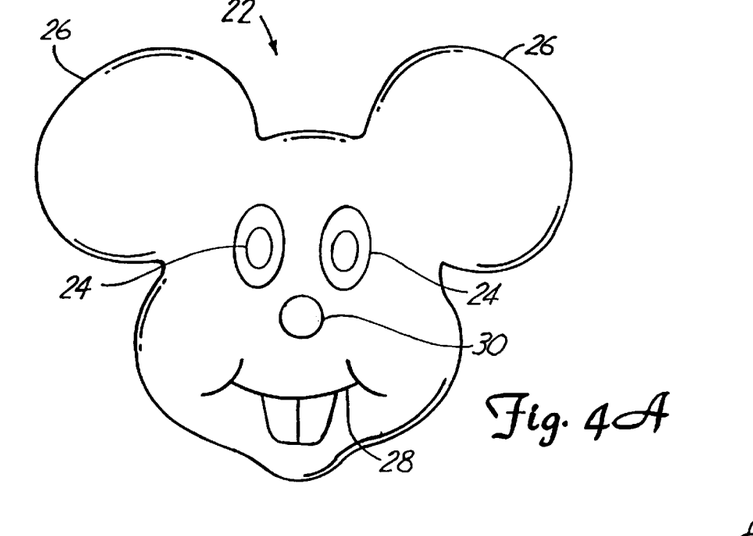
FIG. 4A is a front view of the mask used in a first embodiment of the invention.
Figures 4B, 4C:
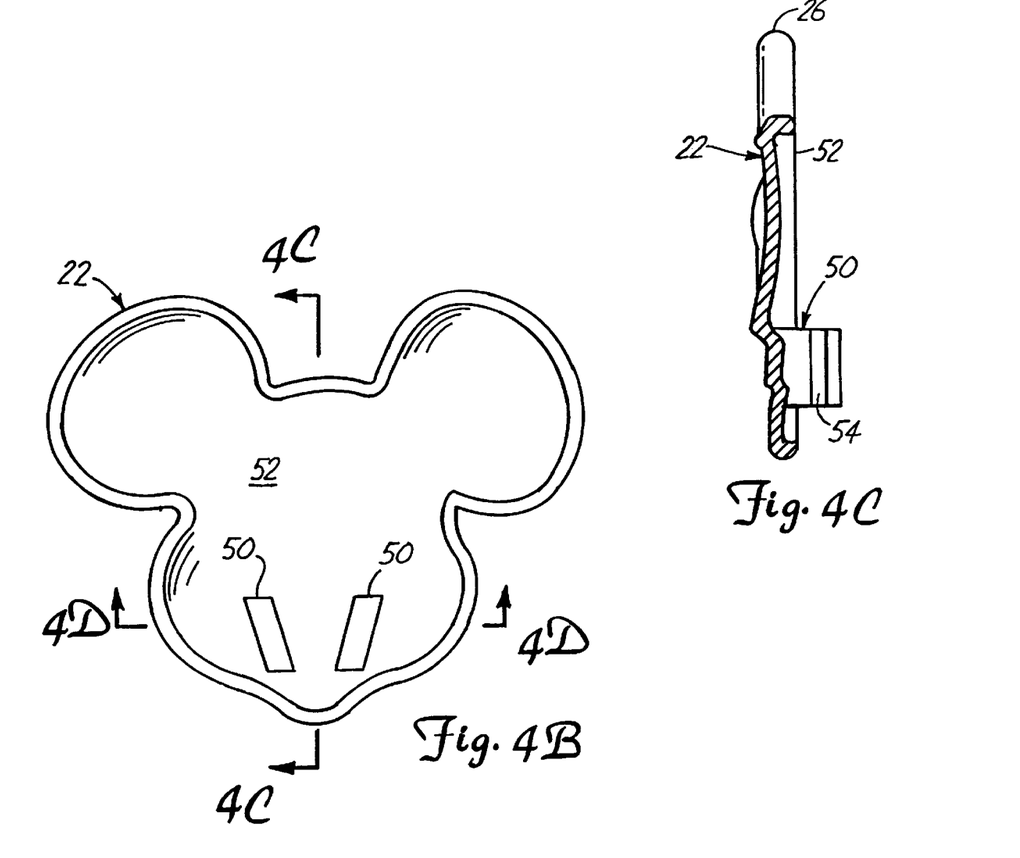
FIG. 4B is a back view of the mask used in the first embodiment of the invention.
FIG. 4C is a side sectional view of the mask through a section 4C—4C of FIG. 4B.

FIGS. 4A–4D illustrate a front, a back, a side sectional and a bottom sectional view, respectively, of the mask 22 used in a preferred embodiment of the invention. FIG. 4A illustrates a front view of the mask 22 that is provided to a child during an examination using the ophthalmoscope attachment 10. The mask 22 will be in front of the child during the examination and thus presents them with an inviting and friendly appearance to look at, such as the smiling face of a mouse. The child will be looking directly at the mask 22 and see the pair of ears 26, the eyes 24, the mouth 28 and the nose 30. These features in particular will help calm any fears or anxiety the child may be experiencing as a result of the ophthalmoscope 12. Once the child's fear and anxiety of the device has subsided, light is emitted through the eyepiece 32 while the child focuses their direct line of sight toward the mask 22 and thus the ophthalmoscope 12 enabling a proper examination of their eye.

Figure 4D:
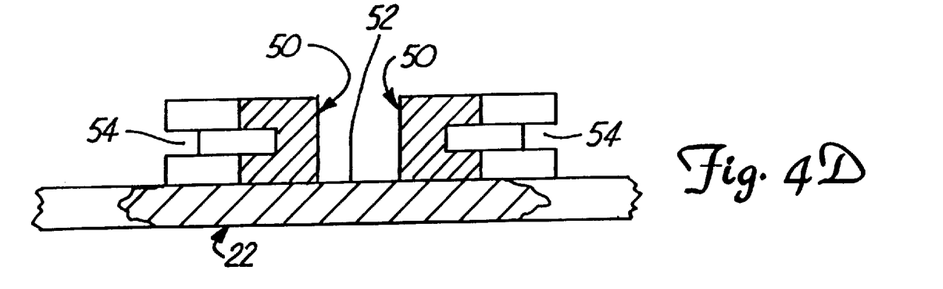
FIG. 4D is a bottom sectional view of the mask through a section 4D—4D of FIG. 4B.

In a preferred embodiment, the mask 22 is secured to the housing 18 by mounting means 36. Mounting means 36 preferably includes a pair of slotted walls 50 that extend from a back 52 of the mask 22 as illustrated in FIG. 4D. The slotted wall 50 preferably provides a track 54 that slides onto the rails 43 on the walls 40 that extend from the mounting plate 38. Once the slotted wall 50 is secured to the rails 43, the mask 22 is secured to the mounting plate 38, which is secured to the housing 18. Once the slotted wall 50 is secured to the rails 43, the bottom of the mask 22 is located just above the eyepiece 32. This avoids blocking any field of view through the ophthalmoscope 12. Once the mask 22 is secured to the rails 43 it will also extend back at an angle of approximately 10 degrees from the vertical line B of FIG. 3B. In a preferred embodiment, the mask 22 has a width of approximately one and one half inches from one side to another, and a height of approximately one and one half inches. The slotted walls 50 extend perpendicularly approximately 3.2 millimeters from the back 52 of the mask 22. The slotted walls 50 are preferably approximately 8.5 millimeters long. The track 54 is preferably just larger than the rails 43 to allow them to fit therein. The slotted walls 50 also preferably slant inward or are closer to each other near the bottom of the mask 22 than at the top. The slotted walls 50 thus form a partial V-shape similar to the walls 40 of the mounting plate 38. The mask 22 is preferably made from a polyvinyl chloride. The mask 22 can be painted or dyed with either characteristic or alternative colors to its general shape to create an inviting and familiar view.

Figure 5:
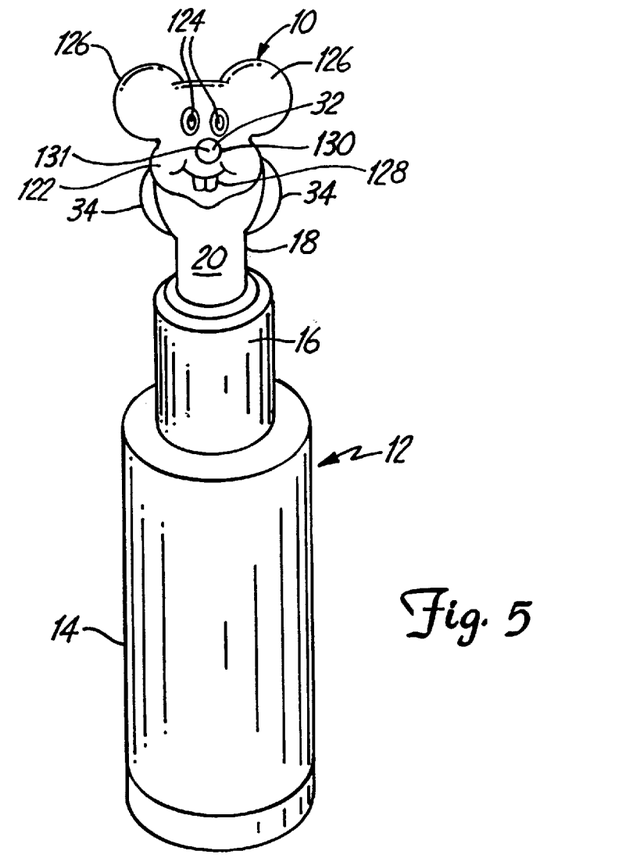
FIG. 5 is a perspective view of a second embodiment of the invention secured to the ophthalmoscope.

A second embodiment of the ophthalmoscope attachment 10 can also be secured to the ophthalmoscope 12. FIG. 5 illustrates the second embodiment of the ophthalmoscope attachment 10 secured to the ophthalmoscope 12. In FIG. 5, the second embodiment of the ophthalmoscope attachment 10 includes a mask 122 secured across the front 20 of the ophthalmoscope 12. Similar to the first embodiment, the mask 122 preferably has a shape of a head of an animal to include a pair of ears 126, a set of eyes 124, a mouth 128, and a nose 130. The mask 122 is illustrated in FIG. 5 in the shape of a mouse head but can have alternative shapes as well, similar to the mask 22.

The second embodiment of the ophthalmoscope attachment 10 preferably also includes an aperture 131 through the mask 122. The aperture 131 is positioned through the mask 122 so that the aperture 131 is aligned with the eyepiece 32 of the ophthalmoscope 12 when the mask 122 is secured across the front 20 of the ophthalmoscope 12. The aperture 131 allows the examining physician or medical personnel to view the patient's eye through the mask 122 secured across the front 20 of the ophthalmoscope 12. The aperture 131 is preferably located as the nose 130.

Figure 6A:
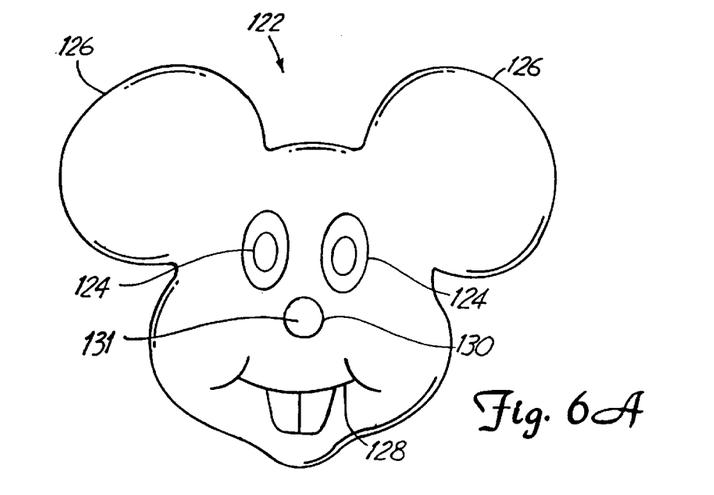
FIG. 6A is a front view of the mask used in a second embodiment of the invention.

FIGS. 6A–6D illustrate a front, a back, a side sectional, and a bottom sectional view, respectively, of the mask 122. FIG. 6A illustrates the view a child will see during an eye examination with the mask 122 secured across the front 20 of the ophthalmoscope 12. The child will again see the pair of ears 126, the pair of eyes 124, and the mouth 128. These features will help calm the child's fear or anxiety as a result of the ophthalmoscope 12, similar to the mask 22. To further assist in subsiding the child's uneasiness of the device, the light within the ophthalmoscope 12 can be turned on and emitted through the eyepiece 32 and aperture 131 to help focus the child's direct line of sight at the mask 122. This allows the examining physician or medical personnel to properly perform the examination of their eye. The child will be curious of and intrigued by the light emitted from what appears to be the nose 130 of the mouse. This will tend to cause the child to stare directly at the light emitting from the aperture 131, or at the nose area 130. The child will tend to continue looking at the aperture 131 until the ophthalmoscope 12 with the ophthalmoscope attachment 10 is removed from the child's sight, or the light emitted through the eyepiece 32 and the aperture 131 is turned off.

Figure 6B:
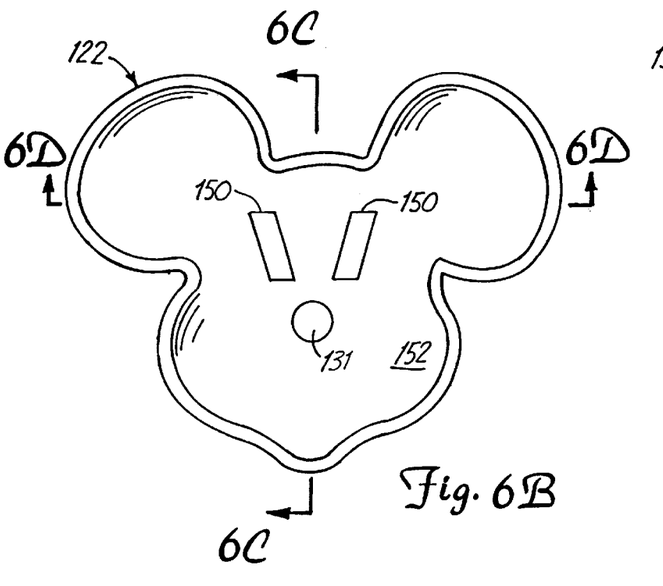
FIG. 6B is a back view of the mask used in the second embodiment of the invention.
Figure 6C:
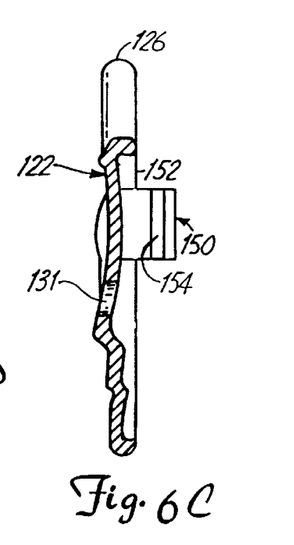
FIG. 6C is a side sectional view of the mask through a section 6C—6C of FIG. 6B.
Figure 6D:
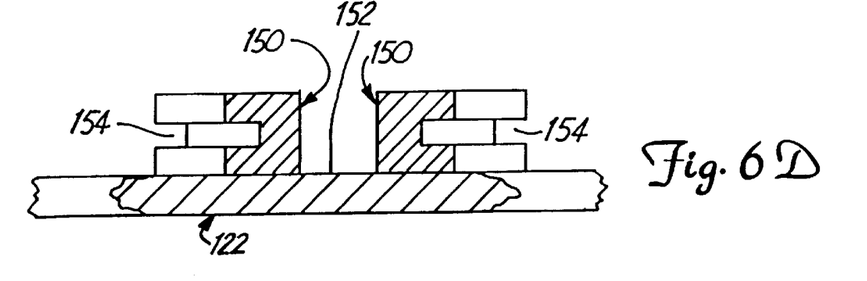
FIG. 6D is a bottom sectional view of the mask through a section 6D—6D of FIG. 6B.

As illustrated in FIGS. 6B to 6D, the mask 122 also includes a pair of slotted walls 150 that extend from a back 152 of the mask 122 and includes a track 154. The track 154 receives the rails 43 mounting the mask 122 to the mounting plate 38 secured to the housing 18 of the ophthalmoscope 12. The slotted walls 150 are similar to the slotted walls 50 of the first embodiment of the mask 22. However, the slotted walls 150 are positioned relative to the aperture 131 through the mask 122 so that when the mask 122 is secured to the ophthalmoscope 12 the aperture 131 is aligned with the eyepiece 32. This results in the slotted walls 150 being located nearer a top of the back 152 of the mask 122 than the location of the slotted walls 50 which are nearer the bottom of the back 52 for the mask 22. The mask 122 is thus secured to the front 20 of the ophthalmoscope 12 similar to the mask 22.

The aperture 131 may be difficult to align with the eyepiece 32 because ophthalmoscopes 12 do not have a uniform placement of the eyepiece 32 relative to the top of their housing 18. Thus the securing means 36, and in particular the mounting plate 38, is not uniformly secured to the ophthalmoscope 12 in relation to the eyepiece 32. To accommodate the various ophthalmoscopes and ensure the aperture 131 is aligned with the eyepiece 32 once the mask 122 is secured to the mounting plate 38, the adhesive strips 44 can be altered to customize their thickness for the various ophthalmoscopes 12 and universalize the relative position of the rails 43 to the eyepiece 32. Alternatively, the slotted walls 150 can be positioned relative to the aperture 131 as required for each different type of ophthalmoscope 12 to ensure proper alignment between the eyepiece 32 and the aperture 131.

Figure 7A:
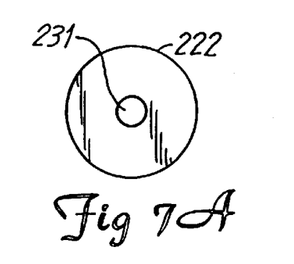
FIGS. 7A–7G are front views of alternative designs for a mask.

FIGS. 7A–7G illustrate alternative features, other than an animal, that the mask 22 can incorporate. For example, as illustrated in FIG. 7A, a mask 222 can have a circular shape and be painted appropriately to resemble either a sun, a moon, or a ball. The mask 222 can further include an aperture 231 in its center that when secured to the ophthalmoscope 12 would be aligned with the eyepiece 32. Thus when the light from the ophthalmoscope 12 is energized it would appear to emanate from the center of the mask 222 through the aperture 231 and appear to give off light as the sun does.

Figure 7B:
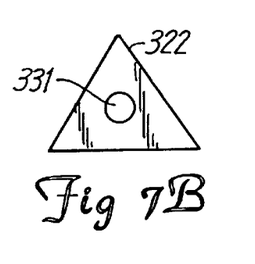

FIG. 7B illustrates a mask 322 in the shape of a triangle. The mask 322 in the shape of a triangle could be decorated to resemble a wedge of cheese, a piece of pie or a piece of pizza. An aperture 331 could be placed in the mask 322 if the mask 322 would otherwise block the eyepiece 32 when it is positioned across the front 20 of the ophthalmoscope 12.

Figure 7C:
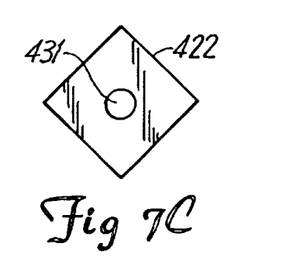

FIG. 7C illustrates a mask 422 in the shape of a diamond. The mask 422 could be decorated as a kite and include an aperture 431 if it were placed across the front 20 of the ophthalmoscope 12 such that it would obscure the view through the eyepiece 32.

Figure 7D:
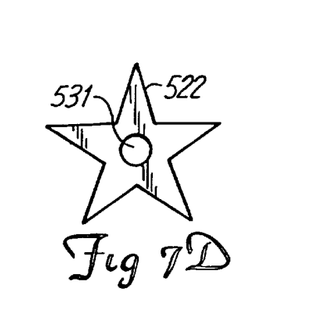

FIG. 7D illustrates a mask 522 in the shape of a star. An aperture 531 could also be placed if necessary in the mask 522 to prevent obscuring the view through the eyepiece 32 when the mask 522 is attached to the ophthalmoscope 12.

Figure 7E:
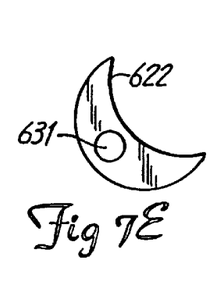

FIG. 7E illustrates a mask 622 in the shape of a crescent. The mask 622 could resemble a moon and be decorated accordingly. An aperture 631 can be placed in the mask 622 if necessary depending upon whether the mask 622 is secured across the front of the ophthalmoscope 12 such that it would cover the view through the eyepiece 32.

Figure 7F:
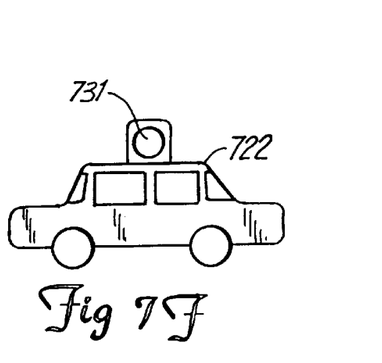

FIG. 7F illustrates a mask 722 in the shape of an emergency vehicle, such as a police car. Similarly, an ambulance or fire truck could also be used. An aperture 731 could be placed in the mask 722, if the mask 722 would otherwise cover the eyepiece 32 of the ophthalmoscope 12 when it is secured to the housing 18. The aperture 731 is preferably incorporated as the emergency lights of the vehicle.

Figure 7G:
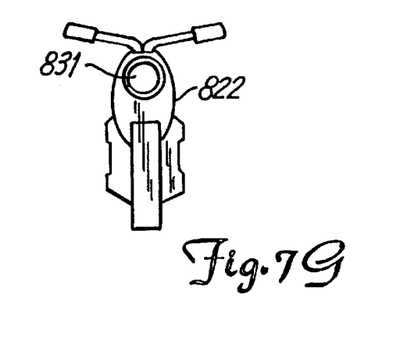

FIG. 7G illustrates that a mask 822 can also be in the shape of a motorcycle. The mask 822 could also include an aperture 831 positioned as a headlight of the motorcycle for alignment with the eyepiece 32 of the ophthalmoscope 12 if necessary.

In FIGS. 7A–7G an aperture has been placed in each alternative design for the mask. However, the aperture would only be necessary if the respective masks were positioned across the front 20 of the ophthalmoscope 12 such that they would cover or obscure the view through the eyepiece 32. Otherwise, if the respective masks are secured to the ophthalmoscope 12 similar to the mask 22 shown in FIG. 1, then the masks would be secured above the eyepiece 32 and no apertures would be necessary or would have to be incorporated.

Although the present invention has been described with reference to preferred embodiments, workers skilled in the art will recognize that changes may be made in form and detail without departing from the spirit and scope of the invention. For instance, the mask can be shaped with a different animal face than a mouse, or alternatively have a geometrical, a vehicular or other child friendly and inviting shape. The size of the mask can also vary to either partially or completely cover the front of the housing. The mounting means could also be incorporated as part of the ophthalmoscope. An alternative technique to secure the mask to the front of the housing, can be substituted as well. These techniques include sliding the mask over the top of the housing, using a clip or a slot or some other similar technique. By use of the ophthalmoscope attachment, children will be more apt to cooperate during an eye examination and look at the eyepiece of the ophthalmoscope as a result of overcoming their fear and anxiety of the device.

What is claimed is:

1. An ophthalmoscope attachment to focus an individual's direction of sight toward a front of an ophthalmoscope near an eyepiece in a housing of the ophthalmoscope, the ophthalmoscope attachment comprising a mask that is secured across the front of the housing of the ophthalmoscope; and mounting means for securing the mask to the housing of the ophthalmoscope.

2. The ophthalmoscope attachment of claim 1, wherein the mounting means comprises:

a mounting plate having a similar shape to the housing above the eyepiece;

an adhesive strip that secures the mounting plate to the housing above the eyepiece;

a pair of opposed facing walls extending out from a front of the mounting plate, each of the walls having a rail; and a pair of opposed facing walls extending from a back of the mask, each of the walls having a track that mates with one of the rails securing the mask to the mounting plate.

3. The ophthalmoscope attachment of claim 2, wherein the mounting plate mirrors the shape of the housing and is made of formed hard plastic that is black in color.

4. The ophthalmoscope attachment of claim 2, wherein the mounting plate has an opening aligned with the eyepiece in the housing to maintain an unobstructed view through the eyepiece of the ophthalmoscope.

5. The ophthalmoscope attachment of claim 1, wherein the ophthalmoscope attachment further includes an aperture through the mask that is aligned with the eyepiece of the ophthalmoscope when the mask is secured across the front of the housing.

6. The ophthalmoscope attachment of claim 1, wherein the mask is made of polyvinyl chloride.

7. The ophthalmoscope attachment of claim 1, wherein the mask includes facial features of an animal.

8. The ophthalmoscope attachment of claim 1, wherein the mask includes features of a vehicle.

9. The ophthalmoscope attachment of claim 1, wherein the mask includes a geometrical shape.

10. An ophthalmoscope attachment to focus an individual's line of sight toward an eyepiece at a front of a housing of an ophthalmoscope; the ophthalmoscope attachment comprising:

a mask having facial features of an animal; and mounting means for securing the mask across the front of the housing.

11. The ophthalmoscope attachment of claim 10, wherein the mounting means comprises:

a mounting plate having a similar shape to the housing above the eyepiece;

an adhesive strip that secures the mounting plate to the housing above the eyepiece;

a pair of opposed facing walls extending out from a front of the mounting plate, each of the walls having a rail; and a pair of opposed facing walls extending from a back of the mask, each of the walls having a track that mates with one of the rails securing the mask to the mounting plate.

12. The ophthalmoscope attachment of claim 11, wherein the mounting plate mirrors the shape of the housing and is made of formed hard plastic that is black in color.

13. The ophthalmoscope attachment of claim 11, wherein the mounting plate has an opening aligned with the eyepiece in the housing to maintain an unobstructed view through the eyepiece of the ophthalmoscope.

14. The ophthalmoscope attachment of claim 10, wherein the ophthalmoscope attachment further includes an aperture through the mask that is aligned with the eyepiece of the ophthalmoscope when the mask is secured across the front of the housing.

15. The ophthalmoscope attachment of claim 14, wherein the aperture is positioned on the mask as one of the facial features of the animal.

16. The ophthalmoscope attachment of claim 10, wherein the mask is made of polyvinyl chloride.

17. An ophthalmoscope attachment to direct a line of sight from an individual toward a front of an ophthalmoscope at an eyepiece in a housing of the ophthalmoscope; the ophthalmoscope attachment comprising:
   a mask having facial features of an animal and a pair of walls that extend from a back of the mask, wherein a track is placed in the walls; and
   a mounting plate secured to the front of the housing having a pair of walls that extend from a front of the mounting plate and include a rail, wherein the rail mates with the track placed in the walls of the mask to removably secure the mask to the mounting plate.

18. The ophthalmoscope attachment of claim 17, wherein the mounting plate mirrors the shape of the housing of the ophthalmoscope and is made of formed hard plastic that is black in color.

19. The ophthalmoscope attachment of claim 17, wherein the mounting plate has an opening aligned with the eyepiece in the housing to maintain an unobstructed view through the eyepiece of the ophthalmoscope.

20. The ophthalmoscope attachment of claim 17, wherein the mask is made of polyvinyl chloride.

21. The ophthalmoscope attachment of claim 17, wherein the ophthalmoscope attachment includes an aperture through the mask that is aligned with the eyepiece when the mask is secured to the mounting plate.

22. The ophthalmoscope attachment of claim 21, wherein the aperture is positioned on the mask as one of the facial features of the animal.

* * * * *